United States Patent [19]

Brenneman et al.

[11] Patent Number: 4,850,983

[45] Date of Patent: Jul. 25, 1989

[54] STYLET WIRE RETAINER

[75] Inventors: Rodney A. Brenneman, Laguna Hills; Charles K. Lovejoy, Tustin, both of Calif.

[73] Assignee: Kendall McGaw Laboratories, Inc., Irvine, Calif.

[21] Appl. No.: 149,462

[22] Filed: Jan. 28, 1988

[51] Int. Cl.$^4$ .............................................. A61M 25/00

[52] U.S. Cl. .................................... 604/270; 604/170; 128/657

[58] Field of Search ................. 604/270, 93, 164, 165, 604/282, 170; 128/657

[56] References Cited

U.S. PATENT DOCUMENTS 4,516,970 5/1985 Kaufmann et al. ................. 604/270

*Primary Examiner*—Stephen C. Pellegrino

*Attorney, Agent, or Firm*—John A. Kane

[57] ABSTRACT

An enteral feeding tube assembly for the administration of fluids to a patient having a semi-rigid stylet guide wire for assisting in the insertion of the feeding tube into the patient's stomach and having a distal orifice for exit of the fluid from the tube. Means are provided for retaining the stylet wire within the tube and restricting access of the end of the stylet wire to the orifice no matter what the size or configuration of the orifice.

8 Claims, 1 Drawing Sheet

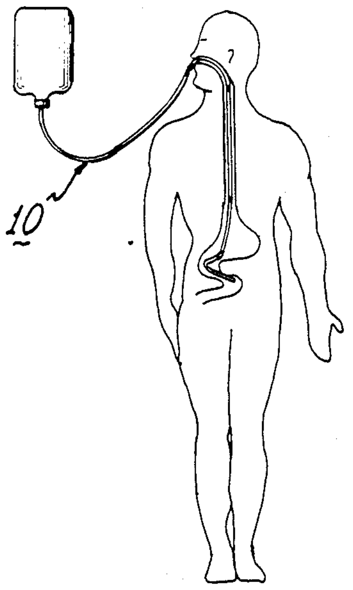
Fig. 1
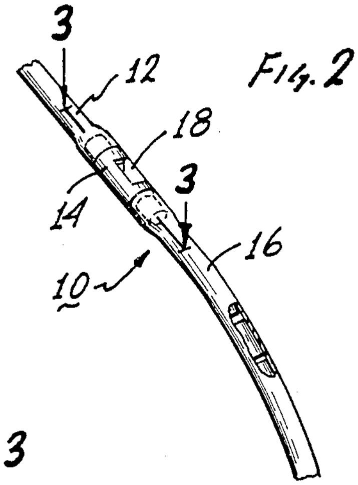
Fig. 2
Fig. 3
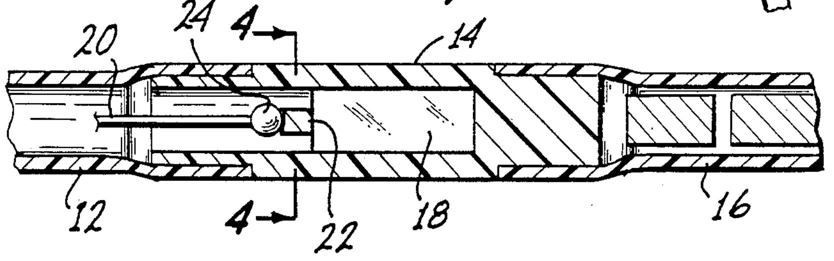
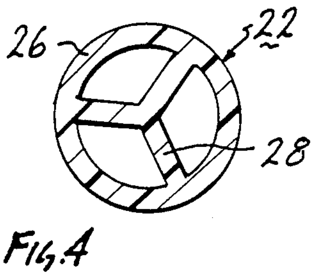
Fig. 4
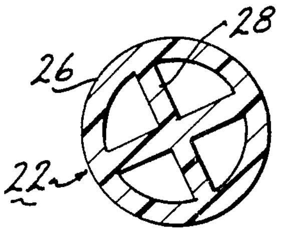
Fig. 5
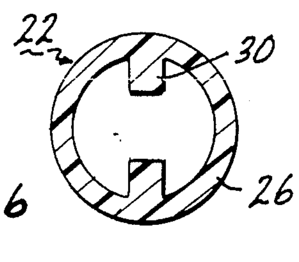
Fig. 6
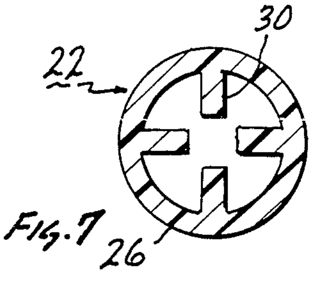
Fig. 7

STYLET WIRE RETAINER

BACKGROUND OF THE INVENTION

I. Field of the Invention

The present invention relates generally to enteral feeding tube assemblies having a stylet wire for guiding the tube into the stomach and more specifically to an improved retaining means for retaining the stylet wire within the tube while providing a larger orifice.

II. Prior Art

Enteral feeding tubes or naso-gastric tubes are well known in the art. Such devices have long been used in feeding compromised patients who are unable to take food orally. The tube provides access through the nasal passage into the stomach or duodenum for the direct administration of liquid nutrition and medication.

The tube generally comprises a weighted distal end for retaining the tube in position in the stomach, a hollow bolus having a distal orifice through which the nutrition is administered, and a tube which extends up through the esophagus through the nasal nasopharynx or oropharynx. The tube is inserted through the nasopharynx and the esophagus with the aid of a stylet guide wire. The stylet wire is placed within the tube up to the distal orifice to provide required rigidity to assist in the insertion of the tube into the stomach.

Most current enteral feeding tubes need such a semi-rigid stylet wire to stiffen the tube enough to permit intubation. The stiff wire poses a serious danger if it is allowed to protrude from the feeding tube, for instance through the hole or holes which comprise the distal orifice. Therefore, in current feeding tubes, these holes are often kept much smaller than the tube inner diameter (and thus smaller than the wire tip). This in turn creates flow difficulties that can lead to tube clogging. Also, smaller holes can more easily be blocked as the tube lies against the stomach wall.

Another attempted solution has been to provide a rigid molded piece with right-angle holes to discourage the protrusion of the stylet wire. Such an interruption in the flow path can result in clogging. Also, the length of the wire will be calculated such that the wire tip should locate within the rigid molded piece entrance section proximal of the holes. However, manufacturing tolerances and/or tube compression during use dictate that the wire tip may end up in (or through) the exit holes within the rigid molded piece. Also, in designing the holes in such a manner as to discourage protrusion of the stylet wire, the holes are down-sized with the result of lower flow capabilities.

An example of a rigid molded piece within an enteral feeding tube of the type described can be found in U.S. Pat. No. 4,490,143. This type of device is an improvement over the prior art design of providing perforations through the wall of the flexible tube itself. However, there can still be clogging problems within the right angle of the flow path and protrusion of the stylet wire is still possible.

SUMMARY OF THE INVENTION

It is therefore the object of the present invention to provide an enteral feeding tube assembly having means for securely retaining a stylet guide wire within the tube and prohibiting protrusion of the stylet wire through the distal orifice of the feeding tube.

It is a further object of the present invention to provide such an enteral feeding tube assembly with a large distal orifice to minimize clogging problems and maximize fluid flow without increasing the risk of protrusion of the stylet guide wire.

Generally, the present invention comprises a rigid or semi-rigid molded hollow bolus which is located between the distal end of the flexible feeding tube and the weighted tip of the feeding tube assembly. The hollow bolus has one or more large cutaway orifices in fluid communication with the interior of the feeding tube. The orifices are designed such that the chance of blockage by contact with the stomach wall or by particles is minimized and that no sharp changes in flow direction are required which might result in clogging of the flow path.

A stylet wire retaining means is provided proximal to the orifice within the bolus such that the tip of the stylet wire is prevented from movement beyond the retaining means thereby eliminating the danger of protrusion through the orifice. This retaining means may comprise one or more inward protrusions from the interior surface of the molded assembly into the flow path such that there is no unobstructed path of greater cross-section than that of the stylet wire tip and thus passage of the stylet wire is prohibited past the protrusions. These protrusions may take the form of one or more inwardly facing bumps or a grid across the flow path. Also, the stylet wire may be provided with an enlarged tip so that the amount of obstruction required for the retaining means can be minimized thus maximizing the flow path.

The present invention, together with additional features and advantages thereof, may be best understood by reference to the following description taken in connection with the accompanying illustrative drawings.

BRIEF DESCRIPTION OF THE DRAWINGS

FIG. 1 is an illustrative diagram showing the placement and insertion of the present invention within a patient together with an enteral feeding bag.

FIG. 2 is a perspective view of the invention showing the distal end of the feeding tube, the molded hollow bolus assembly, and the weighted tip of the feeding tube assembly.

FIG. 3 is a cross-sectional view of the hollow bolus of FIG. 2 taken along lines.

FIG. 4 is a cross-sectional view of the retaining means of the hollow bolus of FIG. 3 taken along line.

FIG. 5 is alternate embodiment of the retaining means of FIG. 4.

FIG. 6 is another alternate embodiment of the retaining means of FIG. 4.

FIG. 7 is yet another alternate embodiment of the retaining means of FIG. 4.

DETAILED DESCRIPTION

Referring now to FIG. 1, one can see the enteral feeding tube assembly 10 of the present invention. FIG. 1 illustrates the method of use of the enteral feeding tube assembly 10. Generally, the enteral feed tube assembly 10 is inserted into the nasal cavity of the patient, passed down through the throat and esophagus into the stomach. A weighted tip on the end of the feeding tube will retain the tube within the stomach or duodenum. Generally, a semi-rigid stylet wire is placed within the feeding tube to assist in the insertion to the esophagus. This stylet wire can then be removed prior to connection of the feeding tube to an enteral feeding bag which contains the nutrient. The nutrient passes through the feeding tube to a distal orifice which is adjacent to the weighted tip, thus permitting flow of the nutrient into the stomach or duodenum.

FIG. 2 illustrates the distal portion of the enteral feeding tube assembly 10 with the hollow tube 12 connected to a hollow bolus 14 which in turn is connected to a weighted tip 16. The hollow bolus 14 is in fluid communication with the interior of the tube 12 with fluid flowing through tube 12 into the hollow bolus 14 and out orifice 18 which is formed in the bolus 14.

Referring next to FIG. 3, one can see a cross-sectional view of the hollow bolus 14 of the present invention. The dimensions of the bolus as well as the hollow tube and weighted tip can vary for different applications, but are well known in the art of enteral feeding tubes. Similarly, the materials used for the tube, the bolus, the weights, and the stylet wire 20 are all well known in the art. FIG. 3 illustrates the placement of the stylet wire 20 during insertion of the enteral feeding tube assembly. During insertion the stylet wire 20 abuts stylet wire retaining means 22 at the proximal end of the bolus 14. An enlarged end such a ball 24 on the tip of the stylet wire 20 can aid in the resistance of the wire 20 penetration past the stylet wire retaining means 22 and through the orifice 18.

The configuration of the stylet wire retaining means 22 will be illustrated more fully in subsequent figures. As can be seen from FIG. 3, the positioning of the stylet wire retaining means 22 is such that the stylet wire is preventing from extending into the bolus 14 and thus prevented from penetrating the orifice 18. Therefore, the orifice 18 may be made quite large with respect to the size of the tube 12. Orifice 18 may be provided on either side of the bolus 14 to provide a clear unhindered flow path from the interior of the tube 12 into the stomach with reduced chances of clogging and limited flow.

Referring next to FIG. 4, one can see a preferred configuration for the stylet retaining means 22 of the present invention. The stylet wire retaining means 22 is molded as part of the proximal end of the bolus 14 which is a single rigid or semi-rigid molded part which may be made out a suitable biocompatible plastic material such as polyurethane or PVC. The configuration shown in FIG. 4 shows a trilateral grid 28 which extends inwardly from the circumference 26 of the stylet wire retaining means 22. This configuration may be selected to provide a maximum flow while still ensuring that the stylet wire will not pass through the openings about the grid 28. This configuration is particularly useful in the case of semi-rigid material being used for the bolus as it resists deformation which could permit passage of the stylet wire. It is also useful for larger diameter feeding tubes where greater coverage of the interior face of the bolus is required.

FIG. 5 shows an alternate grid embodiment for the stylet wire retaining means 22 wherein the grid 28 is in the form of a cross which extends across the mouth of the bolus. This configuration will provide greater coverage of the interior space than that illustrated in FIG. 4, but will also block somewhat more of the fluid flow path.

FIG. 6 illustrates an embodiment which is useful for smaller diameter feeding tubes and/or a bolus made of a more rigid material which resists deformation. In this case, the stylet wire retaining means 22 comprises a plurality of molded protrusions 30 extending inwardly from the circumference 26 of the bolus. In this case, two protrusions 30 are selected to provide the necessary restriction to passage of the stylet wire with a ball tip while maximizing fluid flow.

An alternate embodiment to that shown in FIG. 6 is that of FIG. 7 wherein four molded protrusions 30 are utilized also for a ball ended stylet wire.

Of course, the exact configuration of the grid 28 or molded protrusions 30 is not critical to the present invention. Preferably the configuration and/or number of protrusions will be selected to maximize fluid flow while retaining security from penetration by the stylet wire.

While a wide variety of materials, shapes, and other configurations can be used in this invention, it should be understood that changes can be made without departing from the spirit of scope thereof. This invention, therefore, is not to be limited to the specific embodiments discussed and illustrated herein.

What is claimed is:

1. An enteral feeding tube assembly for enteral administration of fluids to a patient comprising:

a flexible tube configured to be inserted through the nasopharynx or oropharynx, to the stomach of the patient wherein the tube has a proximal end with means for connection to a fluid container and a distal end for insertion into the patient;

a hollow bolus positioned at the distal end of the tube and in fluid communication with the interior of the tube, said hollow bolus having one or more orifices to provide a flow path from the interior of the tube through the hollow bolus to the exterior of the bolus;

a weighted tip positioned distal to said bolus;

a semi-rigid stylet guide wire removably positioned within the tube to provide added rigidity to the feeding tube assembly and thereby assist in the insertion of the distal end of the flexible tube into the stomach; and means for retaining said stylet guide wire within the interior of the tube and preventing passage of said stylet guide wire through said orifice to the exterior of the tube, said retaining means comprising one or more protrusions positioned at a point proximal to the orifice and configured to extend inwardly from the inner surface of the hollow bolus, thereby partially occluding the flow path from the interior of the tube to the orifice sufficiently to restrict passage of the tip of the stylet guide wire.

2. An enteral feeding tube assembly according to claim 1 wherein said retaining means comprises a pair of opposing protrusions.

3. An enteral feeding tube assembly according to claim 1 wherein said retaining means further comprises four opposing protrusions positioned approximately 90 degrees apart around the circumference of the inner surface of the hollow bolus.

4. An enteral feeding tube assembly according to claim 1 wherein said retaining means further comprises a grid positioned across the flow path through the hollow bolus.

5. An enteral feeding tube assembly according to claim 4 wherein said grid comprises a single bar spanning the flow path through the hollow bolus.

6. An enteral feeding tube assembly according to claim 4 wherein said grid has a trilateral configuration comprising three bars having outer ends spaced at approximately 120 degree intervals about the inner surface of the hollow bolus and having inner ends meeting at approximately the center of the flow path through the hollow bolus.

7. An enteral feeding tube assembly according to claim 4 wherein said grid comprises two bars disposed approximately in a cross configuration and spanning the flow path through the hollow bolus.

8. An enteral feeding tube assembly according to claim 1 wherein said retaining means is molded integrally as part of the hollow bolus.

* * * * *